United States Patent
Ling et al.

(10) Patent No.: US 11,020,324 B2
(45) Date of Patent: Jun. 1, 2021

(54) DUAL-CURING DENTAL COMPOSITIONS WITH HIGH STABILITY

(71) Applicant: James R. Glidewell Dental Ceramics, Inc., Newport Beach, CA (US)

(72) Inventors: Long Ling, Anaheim, CA (US); Yulin Chen, Irvine, CA (US); Yumeng Ma, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 16/285,708

(22) Filed: Feb. 26, 2019

(65) Prior Publication Data

US 2020/0268615 A1  Aug. 27, 2020

(51) Int. Cl.
| | |
|---|---|
| *A61K 6/887* | (2020.01) |
| *A61K 6/30* | (2020.01) |
| *A61K 6/61* | (2020.01) |
| *A61K 6/76* | (2020.01) |
| *A61K 6/77* | (2020.01) |

(52) U.S. Cl.
CPC .............. *A61K 6/887* (2020.01); *A61K 6/30* (2020.01); *A61K 6/61* (2020.01); *A61K 6/76* (2020.01); *A61K 6/77* (2020.01)

(58) Field of Classification Search
CPC ..................................................... A61K 6/887
See application file for complete search history.

(56) References Cited

U.S. PATENT DOCUMENTS

| | | | |
|---|---|---|---|
| 6,660,784 B2 | 12/2003 | Ibaragi et al. | |
| 7,166,651 B2 | 1/2007 | Qian | |
| 7,275,932 B2 | 10/2007 | Jin et al. | |
| 7,351,753 B2 | 4/2008 | Qian | |
| 7,498,367 B2 | 3/2009 | Qian | |
| 8,198,343 B2 | 6/2012 | Liu | |
| 9,889,070 B2 | 2/2018 | Kashiki et al. | |
| 10,137,061 B2 | 11/2018 | Rusin et al. | |
| 2007/0040151 A1* | 2/2007 | Utterodt | A61K 6/50 252/182.13 |
| 2007/0100019 A1 | 5/2007 | Sun | |
| 2012/0059083 A1* | 3/2012 | Tokui | A61K 6/30 523/118 |
| 2018/0078465 A1 | 3/2018 | Chen et al. | |
| 2018/0318178 A1 | 11/2018 | Moszner et al. | |

* cited by examiner

*Primary Examiner* — Michael F Pepitone
(74) *Attorney, Agent, or Firm* — Charles Fowler

(57) ABSTRACT

Two-part dual-curing dental compositions containing a hydroperoxide, a thiourea derivative and an acetylacetonate salt as redox radical initiator system, are provided. The dental compositions may contain an acidic monomer for use as a self-adhesive cement. The dental compositions possess enhanced shelf-life stability for working/setting time, bonding strength, color stability, slump, flexural strength/modulus, and when kept at 50° C. for more than 16 weeks.

17 Claims, No Drawings

DUAL-CURING DENTAL COMPOSITIONS WITH HIGH STABILITY

BACKGROUND

Curable polymer compositions are known for use in dental applications, such as for use in resin composites, cements, adhesives and impression materials. Bonding an indirect dental restoration, such as an inlay, onlay, or crown, to a dental surface usually involves employing dental cements, which may be self-adhesive or which require a separate adhesive system. Self-adhesive compositions provide bonding between a dental restoration and a dental structure without pretreating the dental structure surface with a primer or bonding agent. Self-adhesive cements containing acidic monomers may be preferentially used over traditional resin-modified glass ionomers or conventional luting resin cements. The addition of acid functional monomers makes dental cement compositions self-etching and self-adhesive, as good bonding may be achieved without separately etching and priming dental surfaces, resulting in less technique sensitivity and lower post-operative sensitivity.

Where self-adhesive cements contain acidic compounds, well-established redox initiator used for self-curing, such as benzoyl peroxide and an aromatic tertiary amine, may not function well in the acidic environment. If amines are protonated, they may lose potency as a reducing agent. Moreover, low thermal stability of benzoyl peroxides may require refrigeration to prevent premature polymerization of the compositions.

Other redox initiators for use in dental cement compositions are known. U.S. Pat. No. 7,275,932, discloses cumene hydroperoxide and acetylthiourea (CHP/ATU) redox initiator that initiate curing of endodontic sealing compositions and have improved shelf-life stability, and have acidic compounds that could fasten curing. U.S. Pat. No. 7,166,651, discloses self-adhesive dental compositions having cumene hydroperoxide and 1-(2-pydridyl)-thiourea (CHP/PTU) redox initiator incorporated with an acidic compound for etching, priming and cementing.

U.S. Pat. No. 8,198,343, discloses cumene hydroperoxide and benzoylthiourea (CHP/BTU) redox initiator as a self-curing initiator system with acidic monomers for self-adhesive cements. U.S. Pat. No. 9,889,070, discloses 1,1,3,3-tetramethylbutyl hydroperoxide (THP) and a substituted cyclic thiourea selected from 4-methyl-2-imidazolidinethione (METU), 4,4-dimethyl-2-imidazolidinethione (DMETU), 4-ethyl-2-imidazolidinethione (EETU), or 4,4-diethyl-2-imidazolidinethione (DEETU) as redox initiator, with vanadyl acetylacetonate (VO(AcAc)$_2$) or copper (II) acetylacetonate (Cu(AcAc)$_2$) to initiate the compositions.

SUMMARY

Two-part, self-curing dental compositions are provided for use in dental applications, such as dental provisional materials, resin composites and dental cements. Two-part systems disclosed herein, may also be dual-curing dental compositions, and include compositions that are suitable for dental cements, including self-adhesive cements and conventional resin cements that require a separate adhesive system.

A two-part dental composition is provided that has a first part comprising a polymerizable monomer and a hydroperoxide compound as an oxidizing agent. A second part comprises a polymerizable monomer, a thiourea derivative as a reducing agent that comprises fluoro or trifluoromethyl substituted phenylthiourea, which as used herein, refers to a thiourea derivative that comprises phenyl, wherein phenyl comprises one or more substituents selected from fluorine and trifluoromethyl, and an acetylacetonate salt. The thiourea derivative may comprise (difluorophenyl)thiourea or [(trifluoromethyl)phenyl]thiourea.

A two-part, dual-curing dental composition is provided that comprises both chemical initiation to activate polymerization, as well as initiation upon exposure to an external energy source. For example, the dental composition may further comprise a photoinitiator or a photopolymerizable component, rendering the dental composition curable upon the application of a light source. A self-adhesive dental composition may further comprise a polymerizable acidic monomer capable of etching hard dental structures, such as enamel or dentin.

A two-part dual-curing, self-adhesive dental composition is provided that has a first part comprising a polymerizable monomer having an acidic functional group, optionally, a polymerizable monomer having no acidic functional group, and a hydroperoxide compound. A second part comprises a polymerizable monomer having no acidic functional group, a composition comprising fluoro or trifluoromethyl substituted phenylthiourea, a photoinitiator system, and an acetylacetonate salt. In a further embodiment, a two-part system dual-curing, self-adhesive dental cement is provided that comprises a catalyst paste comprising, a hydroperoxide compound, a polymerizable acidic monomer, a polymerizable non-acidic monomer, a filler and a stabilizer, and a base paste that comprises a composition comprising fluoro or trifluoromethyl substituted phenylthiourea, a polymerizable non-acidic monomer, an acetylacetonate salt, a photoinitiator, a filler, and a stabilizer.

Advantageously, a dental composition formed as a two-part system comprising a catalyst paste and a base paste may be stored in a dual chamber syringe. The pastes are stored in separate compartments, and may be mixed, e.g., in approximately a 1:1 volume ratio, immediately prior to application; optionally, the pastes may be dispensed through an auto-mixing tip attached to the syringe.

Dual-curing, self-adhesive dental cement compositions comprising the redox initiator, a hydroperoxide compound and a composition comprising fluoro or trifluoromethyl substituted phenylthiourea, demonstrate improved properties when stored for an extended time at room temperature compared to dental compositions that include known benzoyl peroxide/tertiary amine initiator systems. Self-adhesive dental compositions are provided that are stable upon long term storage at high temperatures. For example, dual-curing self-adhesive dental compositions are provided herein that may be stored at approximately 50° C. for at least 16 weeks, maintaining acceptable working time, setting time, and color stability, and optimized flexural strength, flexural modulus and bonding strength.

DETAILED DESCRIPTION

Two-part, self-curing, or dual-curing, dental compositions are provided for use in applications such as, dental provisional materials, resin composites and resin cements. The dental compositions may be suitable for self-adhesive cements and conventional resin cements that require a separate adhesive system.

Self-curing dental compositions may comprise a first part comprising a hydroperoxide compound as an oxidizing agent and a polymerizable monomer, and a second part that comprises a reducing agent comprising fluoro or trifluoromethyl substituted phenylthiourea, a polymerizable-monomer, and an acetylacetonate salt. In a further embodiment, the two-part system is dual-curing, further comprising, for example, a photoinitiator system.

A dual-curing, self-adhesive dental cement is provided that etches, primes and adheres in one step. The composition may comprise a first part comprising a hydroperoxide compound, a polymerizable acidic monomer and, optionally, a polymerizable non-acidic monomer, and a second part that comprises a fluoro or trifluoromethyl substituted phenylthiourea, a polymerizable non-acidic monomer, and an acetylacetonate salt.

A two-part, dual-curable self-adhesive composition may be provided as a paste/paste system, wherein a catalyst paste comprises a hydroperoxide compound, a polymerizable monomer comprising an acidic group, a filler and a stabilizer, and a base paste that comprises a fluoro or trifluoromethyl substituted phenylthiourea containing compound, a polymerizable monomer without an acidic group, an acetylacetonate salt, a filler, a photoinitiator, and a stabilizer.

A self-curing initiator system suitable for use herein that chemically initiates polymerization of polymerizable monomers, comprises hydroperoxide as an oxidizing agent. The oxidizing agent may comprise one or more hydroperoxide-containing compounds such as, cumene hydroperoxide, t-butyl hydroperoxide, p-diisopropylbenzene hydroperoxide, t-amyl hydroperoxide, pinane hydroperoxide, p-menthane hydroperoxide, or 1,1,3,3-tetramethylbutyl hydroperoxide, or combinations thereof. The total concentration of hydroperoxide in the two-part dental composition is sufficient to initiate radical polymerization when mixing the first part and the second part; in one embodiment, the concentration is sufficient to maintain an acceptable working time to apply and/or manipulate the dental composition before curing and bonding occurs. Concentrations of hydroperoxide compound suitable for use herein may be in a range such as, 0.1% by weight to 5% by weight, or 0.3% by weight to 5% by weight, or 0.5% by weight to 4% by weight, or 0.5% by weight to 3% by weight, based on the total weight of the catalyst part, including components such as fillers, resins, and the like.

Reducing agents suitable for use herein include compositions comprising a fluoro or trifluoromethyl substituted phenylthiourea, including combinations thereof. As used herein, fluoro or trifluoromethyl substituted phenylthiourea, refers to a composition comprising a thiourea derivative comprising phenyl, wherein phenyl comprises one or more substituents selected from fluorine and trifluoromethyl. In some embodiments, a reducing agent may comprise (difluorophenyl)thiourea, which by way of example includes, but is not limited to, (2,3-difluorophenyl)thiourea, or a reducing agent may comprise [(trifluoromethyl)phenyl]thiourea, which includes, but is not limited to, [3-(trifluoromethyl)phenyl]thiourea and [4-(trifluoromethyl)phenyl]thiourea. Reducing agents may comprise combinations of more than one fluoro or trifluoromethyl substituted phenylthiourea, such as, combinations of more than one (difluorophenyl)thiourea, or more than one [(trifluoromethyl)phenyl]thiourea, or combinations of (difluorophenyl)thiourea and [(trifluoromethyl)phenyl]thiourea. In addition to fluoro or trifluoromethyl substituted phenylthiourea, reducing agents may comprise other thiourea reducing agents, such as linear and cyclic substituted thiourea reducing agents. The concentration of fluoro or trifluoromethyl substituted phenylthiourea may be in a range such as, 0.1% by weight to 5% by weight, or 0.2% by weight to 3% by weight, or 0.2% by weight to 2% by weight, or 0.2% by weight to 1.5% by weight, or 0.1% by weight to 1% by weight, based on the total weight of the base part including components such as fillers, resins, and the like.

Self-curing, self-adhesive dental compositions may contain a polymerizable acidic monomer. As used herein, acidic monomers refers to monomers having an acidic functional group suitable for etching a hard dental surface, including but not limited to a phosphate group, phosphonic acid group, carboxylic acid group or sulfonic acid group, or combinations thereof. In one embodiment, the catalyst part may comprise a polymerizable, acrylate- or methacrylate-containing monomer comprising an acidic group. Methacryloyloxydecyl phosphate (MDP), glyceryldimethacrylate phosphate (GDM-P), hydroxyethylmethacrylate phosphate (HEMA-P), phenyl methacryloxyethyl phosphate (phenyl-P), dipentaerythritol pentaacrylate phosphate (PENTA-P), bis(hydroxyethylmethacrylate) phosphate (Bis(HEMA)-P), 4-methacryloxyethyl trimellitic acid (4-MET), 10-methacryloxydecyl malonic acid (MAC-10), pyromellitic dianhydride glycerol dimethacrylate adduct (PMGDM), pyromellitic dimethacrylate (PMDM) or pyromellitic dimethacrylate mixture of isomers (PMDM), or combinations of more than one, thereof, may be suitable for use in self-curing and dual-curing dental compositions described herein. Concentrations of polymerizable monomers having acidic functional groups may be in the range of 1% by weight to 20% by weight, or in the range of 1% by weight to 10% by weight, based on the total weight of the catalyst part.

Dental compositions may comprise one or more polymerizable non-acidic monomers. As used herein, non-acidic monomer refers to a monomer without an acidic functional group, such as an acid phosphate, phosphonic acid, carboxylic acid or sulfonic acid group. Both catalyst and base parts may contain a non-acidic monomer, and the non-acidic monomer contained in a catalyst part may be the same or different as non-acidic monomer contained in a base part. Polymerizable non-acid monomers may comprise hydroxyethyl methacrylate (HEMA), hydroxypropyl methacrylate (HPMA), hydroxybutyl methacrylate (HBMA), glycerol monomethacrylate (GMMA), glycerol dimethacrylate (GDMA), pentaerythritol trimethacrylate (PETMA), bisphenol A glycidyl methacrylate (BisGMA), ethyleneglycol di(meth)acrylate (EGDMA), diethyleneglycol dimethacrylate (DEGDMA), triethyleneglycol dimethacrylate (TEGDMA), tetraethyleneglycol dimethacrylate [(PEG) 4DMA], ethoxylated bis phenol A mimethacrylate (EB-PADMA), 1,6-hexanediol dimethacrylate (HDDMA), 1,10-decanediol dimethacrylate (D3MA), neopentyl glycol dimethacrylate (NPDMA), urethane dimethacrylate (UDMA), or trimethylolpropane trimethacrylate (TMPTMA), or combinations of one or more thereof. The concentration of polymerizable non-acidic monomer in the catalyst part may be the same or different as the base part, and the concentration may be, for example, in the range of 5% by weight to 70% by weight, or 10% by weight to 40% by weight, based on the total weight of the individual part.

Catalyst parts and base parts may each comprise a filler, for example, to impart desired mechanical properties to the dental composition. A filler may comprise, for example, fumed silica, colloidal silica, or precipitated silica, silicate glass, aluminosilicate glass, aluminoborosilicate glass, fluoroaluminosilicate glass, bariumaluminosilicate glass, bariumaluminoborosilicate glass, strontiumaluminosilicate glass, bariumfluoroaluminosilicate glass, strontiumfluoroaluminosilicate glass, strontiumzincfluoroaluminosilicate glass, zincaluminosilicate glass, ytterbium fluoride, yttrium fluoride, strontium fluoride, barium fluoride, or combinations of one or more fillers, thereof. Concentration of filler may be, for example, in a range of 20% by weight to 80% by weight, based on the total weight of the catalyst or base paste, or in a range of 50% by weight to 75% by weight, or in the range of 40% by weight to 75% by weight, based on the total weight of the catalyst or base paste. Optionally, the surface of a filler may be treated or coated by a coupling agent, such as 3-(trimethoxysilyl)propyl methacrylate, to promote the interfacial interaction of the filler and resin matrix.

Acetylacetonate salt that works with a reducing agent comprising a fluoro or trifluoromethyl substituted phenylthiourea and an oxidizing agent comprising hydroperoxide to generate radicals that initiate radical polymerization, may be incorporated in the base part. For example, a base part may comprise an acetylacetonate salt, such as, vanadyl acetylacetonate (VO(AcAc)$_2$) or copper (II) acetylacetonate (Cu(AcAc)$_2$), in a concentration in the range of 0.00005% by weight to 0.05% by weight, or 0.0005% by weight to 0.0050% by weight, or 0.001% by weight to 0.003% by weight, based on the total weight of the base part.

Curable dental compositions that self-cure upon mixing through chemical initiation, may also be dual-curing. For example, dental compositions may further comprise an initiator system for curing dental compositions upon the application of an external energy source, including heat or light, such as a blue light source. Known photoinitiator systems for curing dental composites by known technologies in the dental industry may be suitable for use herein. In some embodiments, a photoinitiator may comprise benzoin, acetophonone, diketone, acylphosphine oxide, ketal, diaryliodonium salt, triarylsulfonium salt, or combinations of one or more thereof.

The catalyst part, the base part or both parts, may comprise known a inhibitor and/or stabilizer, such as a UV stabilizer, that inhibits polymerization or that improves color stability. Compositions may include, but are not limited to 2,6-di-(tert-butyl)-4-methylphenol (BHT), 4-methoxyphenol (MEHQ), 2-hydroxy-4-methoxybenzophenone (UV-9), or combinations thereof.

In a two-part system, such as a catalyst paste and base paste system, components may be contained separately, such as in separate compartments of a dual-chamber syringe. Upon mixing the two parts, oxidizing and reducing agents react to form radicals that polymerize the dental composition. In one embodiment, a catalyst paste and a base paste are dispensed through an automixing tip of a dual-chamber syringe, and mixed in a ratio of approximately 1:1 by volume.

Advantageously, dental compositions provided herein, comprising a hydroperoxide and a fluoro or trifluoromethyl substituted phenylthiourea such as (difluorophenyl)thiourea or [(trifluoromethyl)phenyl]thiourea, redox initiator system, remain curable after long-term storage at high temperatures. Dental compositions exhibit good color stability, working time, setting time, bonding strength, and flexural strength and modulus after storing for at least 12 weeks, or at least 16 weeks, at 50° C., when tested according to the methods described herein. Compositions provided herein have a working time greater than 90 seconds and a setting time of less than 10 minutes after 12 weeks, or after 16 weeks, or after 19 weeks, at 50° C., when tested according to the methods described herein.

Test Method

Shear Bond Strength

Shear bond strength to molar dentin was tested in self-cure mode, light-cure mode, and dual-cure mode, as indicated herein. Sample preparation and testing was conducted substantially according to the method provided in ISO 29022 (Notched-edge shear bond strength test)) (2013). Curing condition were as follows. Self-curing samples were cured for 15 minutes at 37° C.; light cured samples were cured for 20 seconds. Samples were dual-cured by first curing for 5 minutes at 37° C., followed by light curing for 20 seconds with light intensity of about 600 mW/cm$^2$.

Working/Setting Time, Flexural Strength, Flexural Modulus, and Color Stability

Samples were prepared and tested according to the test methods provided in ISO4049, Fourth edition, 2009 Oct. 1, for working and setting times, flexural strength, flexural modulus, and color stability (delta E).

Slump

Slump was determined according to the modified method provided in ISO 4823 (1992) as modified for elastomeric impression materials.

Stability Testing-Accelerated Aging

Dual-chamber syringes were filled with catalyst and base pastes, and stored in an oven at 50° C. Samples were tested at an initial time, and removed from the oven for testing at proposed time until samples were depleted.

EXAMPLES

Abbreviations for components used to prepare compositions, are as follows:

BisGMA—bisphenol A glycidyl methacrylate
HEMA—hydroxyethyl methacrylate
UDMA—di-2-methacryloxyethyl 2,2,4-trimethylhexamethylene-dicarbamate
EBPADMA—ethoxylated bisphenol A dimethacrylate with 2 to 4 units of ethoxylation
TEGDMA—triethyleneglycol dimethacrylate
GDMA—glycerol dimethacrylate, mixture of isomers
TMPTMA—trimethylolpropane trimethacrylate
MDP—10-methacryloyloxydecyl dihydrogen phosphate
CQ—camphorquinone
EDMAB—ethyl-4-dimethylamino benzoate
BTPPO—Bis(2, 4, 6-trimethyl benzoyl) phenyl phosphine oxide
CHP—cumene hydroperoxide
BHT—butylated hydroxytoluene
2FPhTU—(2,3-difluorophenyl)thiourea
3-FPhTU—[3-(trifluoromethyl)phenyl]thiourea
4-FPhTU—[4-(trifluoromethyl)phenyl]thiourea
Cu(AcAc)$_2$—copper(II) acetylacetonate
MPTMS—3-(trimethoxysilyl)propyl methacrylate
OX-50-Sil—fumed silica OX-50 silinated with MPTMS
8202—fumed silica treated with a polydimethylsiloxane
FAS-sil—Fluoroaluminosilicate glass silinated with MPTMS
BG-sil—Bariumfluoroaluminosilicate glass silinated with MPTMS
YbF$_3$—ytterbium(III) fluoride powder
WS—working time (in minutes ('), seconds ("))
ST—setting time (in minutes ('), seconds ("))
FS—flexural strength
FM—flexural modulus
SBS—shear bond strength
Delta E (ΔE)—color difference between the aging and fresh samples Base Paste and Catalyst Pastes Compositions Two-part catalyst paste/base paste dental compositions were formulated for self-adhesive dental cement applications. Compositions comprising acidic monomers, non-acidic monomers, fillers, inhibitor/stabilizers, hydroperoxide, photoinitiator system, thioureas, and acetylacetonate salt, used to make the catalyst and three base pastes, are provided in Table 1. The weight percent (% wt) of each component is based on the total weight of the individual catalyst paste or base paste composition. A reducing agent used for each base paste was selected from (2, 3-difluorophenyl)thiourea (2FPhTU), [3-(trifluoromethyl)phenyl]-thiourea (3-FPhTU), and [4-(trifluoromethyl)-phenyl]thiourea (4-FPhTU), as indicated in the table below.

TABLE 1

Catalyst Paste and Base Pastes Formulations.

| component | Catalyst (% wt) | Base 1 (% wt) | Base 2 (% wt) | Base 3 (% wt) |
|---|---|---|---|---|
| BisGMA | 9.954% | 7.078% | 7.078% | 7.078% |
| GDMA | 4.835% | — | — | — |
| TMPTMA | 4.266% | — | — | — |
| HEMA | 5.688% | 2.949% | 2.949% | 2.949% |
| H$_2$O | 0.853% | — | — | — |
| MDP | 2.844% | — | — | — |
| UDMA | — | 8.847% | 8.847% | 8.847% |
| EBPADMA | — | 8.847% | 8.847% | 8.847% |
| TEGDMA | — | 1.475% | 1.475% | 1.475% |
| CQ | — | 0.059% | 0.059% | 0.059% |
| EDMAB | — | 0.177% | 0.177% | 0.177% |
| BTPPO | — | 0.059% | 0.059% | 0.059% |
| BHT | 0.060% | 0.006% | 0.006% | 0.006% |
| CHP | 1.500% | — | — | — |
| F2PhTU | — | 0.501% | — | — |
| 3-FPhTU | — | — | 0.501% | — |
| 4-FPhTU | — | — | — | 0.501% |
| Cu(AcAc)2 | — | 0.002% | 0.002% | 0.003% |

TABLE 1-continued

Catalyst Paste and Base Pastes Formulations.

| component | Catalyst (% wt) | Base 1 (% wt) | Base 2 (% wt) | Base 3 (% wt) |
|---|---|---|---|---|
| BG-Sil | 60.000% | — | — | — |
| FAS-Sil | — | 60.000% | 60.000% | 60.000% |
| OX-50-Sil | 5.000% | 4.000% | 4.000% | 4.000% |
| R202 | — | 1.000% | 1.000% | 1.000% |
| YbF$_3$ | 5.000% | 5.000% | 5.000% | 5.000% |
|  | 100.000% | 100.000% | 100.000% | 100.000% |

Example 1

A two-part dual curing, self-adhesive dental composition was prepared and tested after aging.

Catalyst and Base 1 pastes were separately prepared that contained components listed in Table 1. Base 1 comprised a thiourea, (2,3-difluorophenyl)thiourea (2FPhTU). Catalyst and base pastes were separately filled into a 1:1 ratio dual-barrel syringe and aged at 50° C. for up to 19 weeks. For testing, the two pastes were mixed through an automixing tip by pushing a plunger in the syringe.

Sample compositions were aged at 50° C. for up to 19 weeks, or until sample compositions were depleted. Measurements were obtained for working times (WT) and setting times (ST), reported in minutes (') and seconds ("). Shear bond strength (SBS) to molar dentin (measured for self-cure mode, light-cure mode and dual-cure mode), values are reported as MPa. Flexural strength (FS), reported as MPa, and flexural modulus (FM), reported as GPa, were measured for self-cure modes. Results and standard deviations (s.d.), are provided in Table 2. Slump (reported in cm) and color change (A E) of the compositions, were measured for freshly prepared and aged samples, as reported in Table 2.

TABLE 2

Properties of Catalyst and Base 1 Composition.

| Ex. 1 (50° C.) | WT min./sec. (s.d.) | ST min./sec. (s.d.) | SBS MPa (s.d.) Self-Cure | SBS MPa (s.d.) Light-Cure | SBS MPa (s.d.) Dual-Cure | FS MPa (s.d.) Self-Cure | FM GPa (s.d.) Self-Cure | ΔE | Slump (cm) |
|---|---|---|---|---|---|---|---|---|---|
| Initial | 2' (23") | 3'51" (31") | 11.6 (3.2) | 9.5 (8.2) | 7.6 (3) | 73.4 (5.9) | 5.38 (0.51) | 0.00 | 2.73 |
| 2 wks | 2'11" (8") | 3'20" (13") | 6.2 (1.4) | — | — | — | — | — | — |
| 4 wks | 2'32" (15") | 3'34" (24") | 7.6 (3) | — | — | — | — | — | — |
| 6 wks | 4'19" (47") | 5'12" (47") | 5.3 (1.8) | — | — | — | — | — | — |
| 8 wks | 4'18" (22") | 5'17" (21") | 4.1 (1.6) | — | — | — | — | — | — |
| 10 wks | 3'7" (12") | 4'7" (15") | 3.7 (2) | 5.2 (1.3) | 7.6 (5.7) | 113.9 (8.8) | 7.21 (0.49) | 1.52 | — |
| 12 wks | 7'35" (58") | 7'55" (51") | 7.4 (2.4) | 7.3 (2) | 9.4 (4.8) | 101.4 (10.0) | 5.92 (0.76) | 2.40 | 2.7 |
| 14 wks | 4'43" (4") | 5'5" (7") | 5.5 (2.1) | — | — | — | — | 2.95 | — |
| 16 wks | 6'7" (14") | 6'33" (15") | 2.6 (1.6) | — | — | — | — | — | — |
| 17 wks | 7'30" (14") | 7'55" (7") | 1.6 (0.2) | — | — | — | — | — | — |
| 18 wks | 3'27" (21") | 4'3" (21") | 4.4 (2.5) | — | — | — | — | — | — |
| 19 wks | 4'50" | 5'10" | — | — | — | — | — | — | — |

Sample compositions of Example 1 exhibited good stability at 50° C. throughout the testing period which continued until compositions were depleted. For example, working time (WT) and setting time (ST) were 4'50" and 5'10" after aging for 19 weeks, compared to initial WT 2' and ST 3'51", respectively. The change in color (ΔE) was less than 3 after aging for 14 weeks. After aging for 12 weeks, shear bond strength was 7.4 MPa for self-cure and 7.3 MPa for light-cure, SBS of dual-cure was 9.4 MPa. Flexural strength (FS) increased after 12 weeks, compared to initial time. There was almost no change in slump.

Example 2

A two-part dual curing, self-adhesive dental composition was prepared and tested after aging.

Catalyst and Base 2 pastes were prepared comprising the components listed in Table 1. Base 2 comprised a thiourea, [3-(trifluoromethyl)phenyl]thiourea (3-FPhTU). Catalyst and Base 2 pastes were separately filled into a 1:1 ratio dual-barrel syringe and aged at 50° C. for up to 16 weeks. For testing, the two pastes were mixed through an automixing tip by pushing a plunger in the syringe.

Measurements were obtained for working times (WT) and setting times (ST), reported in minutes (') and seconds ("). Shear bond strength (SBS) to molar dentin values (measured for self-cure mode, light-cure mode and dual-cure mode) are reported as MPa. Flexural strength, reported as MPa, and flexural modulus (FM), reported as GPa, were measured for self-cure modes. Results and standard deviations (s.d.), are provided in Table 3. Slump, reported in (cm), and color change (ΔE) of the compositions, are reported in Table 3.

TABLE 3

Properties of Catalyst and Base 2 Composition.

| Ex. 2 (50° C.) | WT min./sec. (s.d.) | ST min./sec. (s.d.) | SBS MPa (s.d.) | | | FS MPa (s.d.) | PM GPa (s.d.) | ΔE | Slump (cm) |
| --- | --- | --- | --- | --- | --- | --- | --- | --- | --- |
| | | | Self-Cure | Light-Cure | Dual-Cure | Self-Cure | Self-Cure | | |
| Initial | 1'55" (17") | 3'14" (14") | 5.8 (2) | 6.6 (5.6) | 7.8 (3.2) | 98.3 (8.1) | 7.28 (0.33) | — | 3.03 |
| 2 wks | 2'53" (14") | 3'54" (22") | 3.6 (0.9) | — | — | — | — | — | — |
| 4 wks | 3'57" (23") | 5'53" (15") | 9.2 (6.6) | — | — | — | — | — | — |
| 6 wks | 2'57" (19") | 4'27" (23") | 3.8 (1.9) | — | — | — | — | — | 2.93 |
| 8 wks | 3'30" (22") | 4'17" (40") | 3.8 (2) | — | — | — | — | — | — |
| 10 wks | 3'19" (10") | 4'27" (25") | 6.4 (1.1) | 5.6 (2) | 4.7 (2.2) | 98.7 (13.8) | 7.12 (0.49) | 1.14 | — |
| 12 wks | 4'42" (13") | 5'8" (20") | 5.1 (3.1) | 8.8 (6.5) | 8.3 (3.7) | 92.5 (23.8) | 6.81 (0.54) | 1.63 | 2.65 |
| 14 wks | 9'25" (15") | 9'50" (17") | 4.6 (2.2) | — | — | — | — | — | — |
| 16 wks | 5'53" (21") | 6'13" (21") | 4.5 (1.7) | — | — | — | — | — | — |

Sample compositions of Example 2 also showed good stability at 50° C. throughout the testing period. For example, working time (WT) and setting time (ST) were 5'53" and 6'13", respectively, after 16 weeks at 50° C. Color difference measurements (ΔE) were less than 2 after aging for 12 weeks. After aging for 12 weeks, shear bond strength (SBS) remained about the same and for self-cure SBS was 5.1 MPa, 8.8 MPa for light-cure and 8.3 MPa for dual-cure.

Example 3

A two-part dual curing, self-adhesive dental composition was prepared and tested after aging.

A catalyst paste was provided having the same formulation as described in Example 1, according to the composition of Table 1. Base 3 paste was prepared using [4-(trifluoromethyl)phenyl]thiourea (4-FPhTU) as the thiourea according to the composition of Table 1. The catalyst and Base 3 pastes were separately filled into a 1:1 ratio dual-barrel syringe, and aged at 50° C. for up to 16 weeks. For testing, the two pastes were mixed through an automixing tip by pushing a plunger in the syringe.

Measurements were obtained for working times (WT) and setting times (ST), reported in minutes (') and seconds ("). Shear bond strength (SBS) to molar dentin values (measured for self-cure mode, light-cure mode and dual-cure mode) are reported as MPa. Flexural strength, reported as MPa, and flexural modulus (FM), reported as GPa, were measured for self-cure modes. Results and standard deviations (s.d.), are provided in Table 4. Color change (delta E) values of the compositions are reported in Table 4.

TABLE 4

Properties of Catalyst and Base 3 Combinations.

| EX. 3 (50° C.) | WT min./sec. (s.d.) | ST min./sec. (s.d.) | SBS MPa (s.d.) | | | FS MPa (s.d.) | FM GPa (s.d.) | ΔE |
|---|---|---|---|---|---|---|---|---|
| | | | Self-Cure | Light-Cure | Dual-Cure | Self-Cure | Self-cure | |
| Initial | 1'58" (11") | 3'34" (8") | 5.6 (27) | 9.58 (2.82) | 9.63 (5.96) | 97.6 (15.9) | 7.36 (0.35) | — |
| 2 wks | 1'53" (14") | 3'28" (13") | 5.80 (2.66) | 6.60 (2.89) | 9.10 (2.69) | 108.3 (17.7) | 7.56 (0.31) | — |
| 4 wks | 1'54" (13") | 3'18" (15") | 4.78 (1.28) | 6.13 (1.61) | 8.74 (4.68) | 99.6 (16.7) | 7.79 (0.46) | — |
| 6 wks | 1'58" (14") | 3'43" (24") | 5.92 (3.60) | 9.47 (4.18) | 8.11 (2.83) | 107.7 (13.5) | 7.72 (0.36) | 1.32 |
| 8 wks | 2'27" (23") | 4'14" (31") | 5.12 (0.82) | 6.19 (2.87) | 6.30 (2.65) | 106.9 (25.9) | 7.55 (0.16) | — |
| 10 wks | 3'10" (17") | 5' (7") | 3.89 (1.07) | 6.28 (2.67) | 4.65 (1.08) | 100.6 (13.4) | 7.72 (0.43) | — |
| 12 wks | 3'3" (22") | 5'2" (30") | 2.92 (0.75) | 4.97 (2.65) | 7.62 (2.07) | 114.1 (11.8) | 7.62 (0.40) | 0.60 |
| 14 wks | 2'12" (13') | 4'26" (17") | 5.41 (2.95) | 7.69 (3.29) | 6.29 (2.46) | | | — |
| 16 wks | — | — | 2.32 (1.93) | 8.04 (4.16) | 8.79 (1.76) | 76.9 (13.3) | 5.43 (0.28) | 0.97 |

Sample compositions of Example 3 showed good stability at 50° C. throughout the testing period, which continued until compositions were depleted. There were no significant changes between the initial test and aged samples, for example, for working time (WT) and setting time (ST) and color difference (ΔE) measurements were less than 2 after aging for 12 and 16 weeks.

We claim:

1. A two-part curable dental composition comprising
a) a first part comprising
   a polymerizable monomer having an acidic functional group,
   a first polymerizable monomer having no acidic functional group, and
   a hydroperoxide compound; and
b) a second part comprising
   a second polymerizable monomer having no acidic functional group,
   a composition comprising [4-(trifluoromethyl) phenyl] thiourea, and
   an acetylacetonate compound,
wherein the first part, the second part, or both, optionally comprise a filler.

2. The two-part dental composition of claim 1, where the first part is a paste and the second part is a paste.

3. The two-part dental composition of claim 1, wherein the polymerizable monomer having an acidic functional group comprises methacryloyloxydecyl phosphate, glyceryldimethacrylate phosphate, hydroxyethylmethacrylate phosphate, phenyl methacryloxyethyl phosphate (phenyl-P), dipentaerythritol pentaacrylate phosphate, or bis(hydroxyethylmethacrylate) phosphate, or a combination thereof.

4. The two-part dental composition of claim 1, wherein the polymerizable monomer having an acidic functional group comprises 4-methacryloxyethyl trimellitic acid, or 10-methacryloxydecyl malonic acid, or a combination thereof.

5. The two-part dental composition of claim 1, wherein the polymerizable monomer having an acidic functional group has a concentration of 1% by weight to 20% by weight of the first part.

6. The two-part dental composition of claim 1, wherein the hydroperoxide compound comprises cumene hydroperoxide, t-butyl hydroperoxide, p-diisopropylbenzene hydroperoxide, t-amyl hydroperoxide, pinane hydroperoxide, p-menthane hydroperoxide, or 1,1,3,3-tetramethylbutyl hydroperoxide, or a combination thereof.

7. The two-part dental composition of claim 1, wherein the hydroperoxide compound has a concentration of 0.1% by weight to 5% by weight of the first part.

8. The two-part dental composition of claim 1, wherein the second part comprises vanadyl acetylacetonate, vanadium(III) acetylacetonate or copper(II) acetylacetonate, or a combination thereof.

9. The two-part dental composition of claim 1, wherein the first part comprises a filler, and the second part comprises a second filler that is different from the first filler.

10. The two-part dental composition of claim 1, wherein the composition is a dual-curing composition and the second part further comprises a photoinitiator.

11. The two-part dental composition of claim 1, wherein the composition further comprises a stabilizer.

12. A dental device having a two-part dental composition comprising
a dispensing syringe comprising at least two compartments,
a dental composition comprising
   i) a first paste in a first compartment comprising
      a polymerizable acidic monomer,
      a polymerizable non-acidic monomer, and
      a hydroperoxide compound; and
   ii) a second paste in a second compartment that is separated from the first compartment, comprising
      a non-acidic monomer,
      a photoinitiator system,
      a composition comprising [4-(trifluoromethyl) phenyl]thiourea
      an acetylacetonate salt,
wherein the dental composition comprises at least one filler, and
wherein the dental composition, stored for at least 16 weeks at 50° C., is curable upon mixing the first paste and the second paste.

13. The dental device of claim 12, wherein the two-part dental composition, stored for at least 16 weeks at 50° C., has a working time and a setting time of at least 90 seconds and less than 10 minutes.

14. The dental device of claim 12, wherein the two-part dental composition stored for at least 16 weeks at 50° C. has a delta E of less than 3.

15. The dental device of claim 12, wherein the hydroperoxide compound comprises cumene hydroperoxide, t-butyl hydroperoxide, p-diisopropylbenzene hydroperoxide, t-amyl hydroperoxide, pinane hydroperoxide, p-menthane hydroperoxide, or 1,1,3,3-tetramethylbutyl hydroperoxide, or a combination thereof.

16. A curable dental composition comprising
   a) a first paste comprising:
      at least one polymerizable monomer having an acidic functional group,
      at least one polymerizable monomer having no acidic functional group, and
      a hydroperoxide compound; and
   b) a second paste comprising
      at least one polymerizable monomer having no acidic functional group,
      a composition comprising [4-(trifluoromethyl)phenyl]thiourea
      a photoinitiator, and
      an acetylacetonate compound,
   wherein the dental composition further comprises a filler.

17. The curable dental composition of claim 16, wherein the at least one polymerizable monomer having an acidic functional group comprises a phosphate group, a carboxylic acid group, or sulfonic acid group.

* * * * *